US006972173B2

(12) United States Patent
Su et al.

(10) Patent No.: US 6,972,173 B2
(45) Date of Patent: Dec. 6, 2005

(54) METHODS TO INCREASE NUCLEOTIDE SIGNALS BY RAMAN SCATTERING

(75) Inventors: Xing Su, Cupertino, CA (US); Selena Chan, Sunnyvale, CA (US); Andrew A. Berlin, San Jose, CA (US); Tae-Woong Koo, South San Fancisco, CA (US); Narayan Sundararajan, San Francisco, CA (US); Mineo Yamakawa, Campbell, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 10/099,287

(22) Filed: Mar. 14, 2002

(65) Prior Publication Data

US 2003/0186240 A1   Oct. 2, 2003

(51) Int. Cl.[7] .......................... C12Q 1/68; C12P 19/34; C07H 21/02

(52) U.S. Cl. ..................... 435/6; 435/91.2; 536/23.1; 536/24.3; 422/82.08

(58) Field of Search .................. 435/6, 91.2; 422/82.08

(56) References Cited

U.S. PATENT DOCUMENTS

| 4,962,037 | A | 10/1990 | Jett et al. |
|---|---|---|---|
| 5,306,403 | A | 4/1994 | Vo-Dinh |
| 5,405,747 | A | 4/1995 | Jett et al. |
| 5,674,743 | A | 10/1997 | Ulmer |
| 5,707,804 | A | 1/1998 | Mathies et al. |
| 5,721,102 | A | 2/1998 | Vo-Dinh |
| 5,776,674 | A | 7/1998 | Ulmer |
| 5,783,389 | A | 7/1998 | Vo-Dinh |
| 5,814,516 | A | 9/1998 | Vo-Dinh |
| 5,866,336 | A | 2/1999 | Nazarenko et al. |
| 5,867,266 | A | 2/1999 | Craighead |
| 6,002,471 | A | 12/1999 | Quake |
| 6,040,191 | A | 3/2000 | Grow |
| 6,054,495 | A | 4/2000 | Markowitz |
| 6,127,120 | A | 10/2000 | Graham et al. |
| 6,136,543 | A | 10/2000 | Anazawa et al. |
| 6,140,053 | A | 10/2000 | Köster |
| 6,149,868 | A | 11/2000 | Natan et al. |
| 6,174,677 | B1 | 1/2001 | Vo-Dinh |
| 6,180,415 | B1 | 1/2001 | Schultz et al. |
| 6,210,896 | B1 | 4/2001 | Chan |
| 6,214,246 | B1 | 4/2001 | Craighead |
| 6,219,137 | B1 | 4/2001 | Vo-Dinh |
| 6,225,068 | B1 | 5/2001 | Wolfrum |
| 6,313,914 | B1 | 11/2001 | Roe |
| 6,344,272 | B1 | 2/2002 | Oldenburg et al. |
| 6,376,177 | B1 | 4/2002 | Poponin |

FOREIGN PATENT DOCUMENTS

WO     WO 00/70073    11/2000

OTHER PUBLICATIONS

Sauer et al, "Single molecule DNA sequencing in submicrometer channels: state of the art and future prospects",J. Biotechnology (Apr. 2001) 86:181-201.*
Matsuura et al, "Real time observation of a single DNA digestion by lambda exonuclease under a fluorescence microscope field", Nucleic Acids Research (2001) 29:e79.*
Molecular Probes product information, Thiol reactive Probes, MP 00003, Jul. 8, 2003.*
Nanogold Labeling Reagents, Http://www.Nanoprobes.com/Labrgts.html (accessed Aug. 25,2003).*
Machara, N. et al., Efficient Detection of Single Molecules Eluting Off an Optically Trapped Microsphere, *Bioimaging* 6 (1998), 33-42, 1998.
1997 DOE Human Genome Program Contractor-Grantee Workshop VI, pp. 23-25, Retrieved from the Internet URL: <http://www.ornl.gov/hgmis/publicat/97santa/seqtech.html.
M. Sauer, New Strategies for DNA Sequencing Using Diode Laser-Based Time-Resolved Fluorescence Detection [Retrieved on Nov. 12, 2001]. Retrieved from the Internet URL: <http:// pc-cube01.pci.uni-heidelberg.de/alt/msauer/emsproject01.htm. 2 pages.
Lee and Meisel, *J. Phys. Chem.* 86:3391-3395, 1982.
Goodwin et al., 1996, *Acc. Chem. Res.* 29:607-613.
Feldheim, "Assembly of metal nanoparticle arrays using molecular bridges," The Electrochemical Society Interface, Fall, 2001, pp. 22-25.
K. Dörre et al., "Techniques for Single Molecule Sequencing," Bioimaging 5 (1997) 139-152.
B. Dubertret et al., "Single-Mismatch Detection Using Gold-Quenched Fluorescent Oligonucelotides," Nature Biotechnology, vol. 19, 2001, 365-370.
Bloch et al., "Optics with an atom laser beam," *Phys. Rev. Lett.* 87, 2001.

(Continued)

*Primary Examiner*—Jeffrey Fredman
(74) *Attorney, Agent, or Firm*—DLA Piper Rudnick Gray Cary US LLP

(57) ABSTRACT

The methods and apparatus disclosed herein concern nucleic acid sequencing by enhanced Raman spectroscopy. In certain embodiments of the invention, nucleotides are covalently attached to Raman labels before incorporation into a nucleic acid 13. Exonuclease 15 treatment of the labeled nucleic acid 13 results in the release of labeled nucleotides 16, 130, which are detected by Raman spectroscopy. In alternative embodiments of the invention, nucleotides 16, 130 released from a nucleic acid 13 by exonuclease 15 treatment are covalently cross-linked to silver or gold nanoparticles 140 and detected by surface enhanced Raman spectroscopy (SERS), surface enhanced resonance Raman spectroscopy (SERRS) and/or coherent anti-Stokes Raman spectroscopy (CARS). Other embodiments of the invention concern apparatus 10, 100, 210 for nucleic acid sequencing.

7 Claims, 3 Drawing Sheets

OTHER PUBLICATIONS

Ivanisevic et al., "'Dip-Pen'Nanolithography on Semiconductor Surfaces," *J. Am. Chem. Soc.*, 123: 7887-7889, 2001.

Siegel, "Ion Beam Lithography," VLSI Electronics, Microstructure Science, vol. 16, Einspruch and Watts eds., Academic Press, New York, 1987.

Jin et al., "Photoinduced Conversion of Silver Nanospheres to Nanoprisms," Science, 294: 1901-1903, 2001.

Ambrose, W. Patrick et al., "Application of Single Molecule Detection to DNA Sequencing and Sizing", *Ber. Bunseges. Phys. Chem.*, 97(12):1535-1542.

Castro, A. et al., "Fluorescence Detection and Sizing Measurement of Single DNA Molecules," *Analytical Chemistry, American Chemical Society*, 65(7):849-852, Elsevier (1993).

Goodwin, Peter M. et al., "Progress toward DNA sequencing at the single molecule level," *Experimental technique of Physics*, 41 (2):279-294, (1995).

Goodwin, Peter M. et al., "Application of Single Molecule Detection to DNA Sequencing," *Nucleosides and Nucleotides*, 16(5/6)543-550 (1997).

Schecker, Jay A. et al., "Flow-Based Continuous DNA Sequencing Via Single Molecule Detection of Enzymatically Cleaved Fluorescent Nucleotides," *SPIE*, 2386:4-12 (1995).

Szoelloesi, J. et al., "Application of Fluorescence Resonance Energy Transfer in the Clinical Laboratory: Routine and Research," *Cytometry*, 34(4): 159-179 (1998).

Uibel, Rory H. and Harris, Joel M. "Fiber-Optic Raman Spectroscopy for *in Situ* Monitoring of Metal-Ion Complexation by Ligands Immobilized onto Silica Gel," *Applied Spectroscopy*, 54(12):1868-1875 (2000).

Watson, N. et al., "Detection of DNA Sequence by Surface Enhanced Resonance Raman Scattering of a Modified DNA Probe," *Progress in Forensic Genetics*, 7(1167):6-8 (1998).

Weiss, Shimon, "Fluorescence Spectyroscopy of Single Biomolecules" *Science*, 283(5408):1676-1683 (1999).

Matsuura, et al., "Real-time observation of a single DNA digestion by λ exonuclease under a fluorescence microscope field", *Nucleic Acids Research*, vol. 29, No. 16, pp. 1-5, 2001.

"Molecular Probes", *Thiol Reactive probes*, 2003.

Nanogold Labeling reagents, 2002, http:/www.nanoprobes.com/LabRgts.html.

Sauer, et al., "Single molecule DNA sequencing in submicrometer channels: state of the art and future prospects", *J. Biotechnology*, vol. 86, pp. 181-201, 2001.

* cited by examiner

METHODS TO INCREASE NUCLEOTIDE SIGNALS BY RAMAN SCATTERING

FIELD OF THE INVENTION

The present methods and apparatus relate to the fields of molecular biology and genomics. More particularly, the methods and apparatus concern nucleic acid sequencing.

BACKGROUND

Genetic information is stored in the form of very long molecules of deoxyribonucleic acid (DNA), organized into chromosomes. The human genome contains approximately three billion bases of DNA sequence. This DNA sequence information determines multiple characteristics of each individual. Many common diseases are based at least in part on variations in DNA sequence.

Determination of the entire sequence of the human genome has provided a foundation for identifying the genetic basis of such diseases. However, a great deal of work remains to be done to identify the genetic variations associated with each disease. That would require DNA sequencing of portions of chromosomes in individuals or families exhibiting each such disease, in order to identify specific changes in DNA sequence that promote the disease. Ribonucleic acid (RNA), an intermediary molecule in processing genetic information, may also be sequenced to identify the genetic bases of various diseases.

Existing methods for nucleic acid sequencing, based on detection of fluorescently labeled nucleic acids that have been separated by size, are limited by the length of the nucleic acid that can be sequenced. Typically, only 500 to 1,000 bases of nucleic acid sequence can be determined at one time. This is much shorter than the length of the functional unit of DNA, referred to as a gene, which can be tens or even hundreds of thousands of bases in length. Using current methods, determination of a complete gene sequence requires that many copies of the gene be produced, cut into overlapping fragments and sequenced, after which the overlapping DNA sequences may be assembled into the complete gene. This process is laborious, expensive, inefficient and time-consuming.

BRIEF DESCRIPTION OF THE DRAWINGS

The following drawings form part of the present specification and are included to further demonstrate certain aspects of the disclosed embodiments of the invention. The embodiments of the invention may be better understood by reference to one or more of these drawings in combination with the detailed description of specific embodiments of the invention presented herein.

DESCRIPTION OF ILLUSTRATIVE EMBODIMENTS

Figure 1:
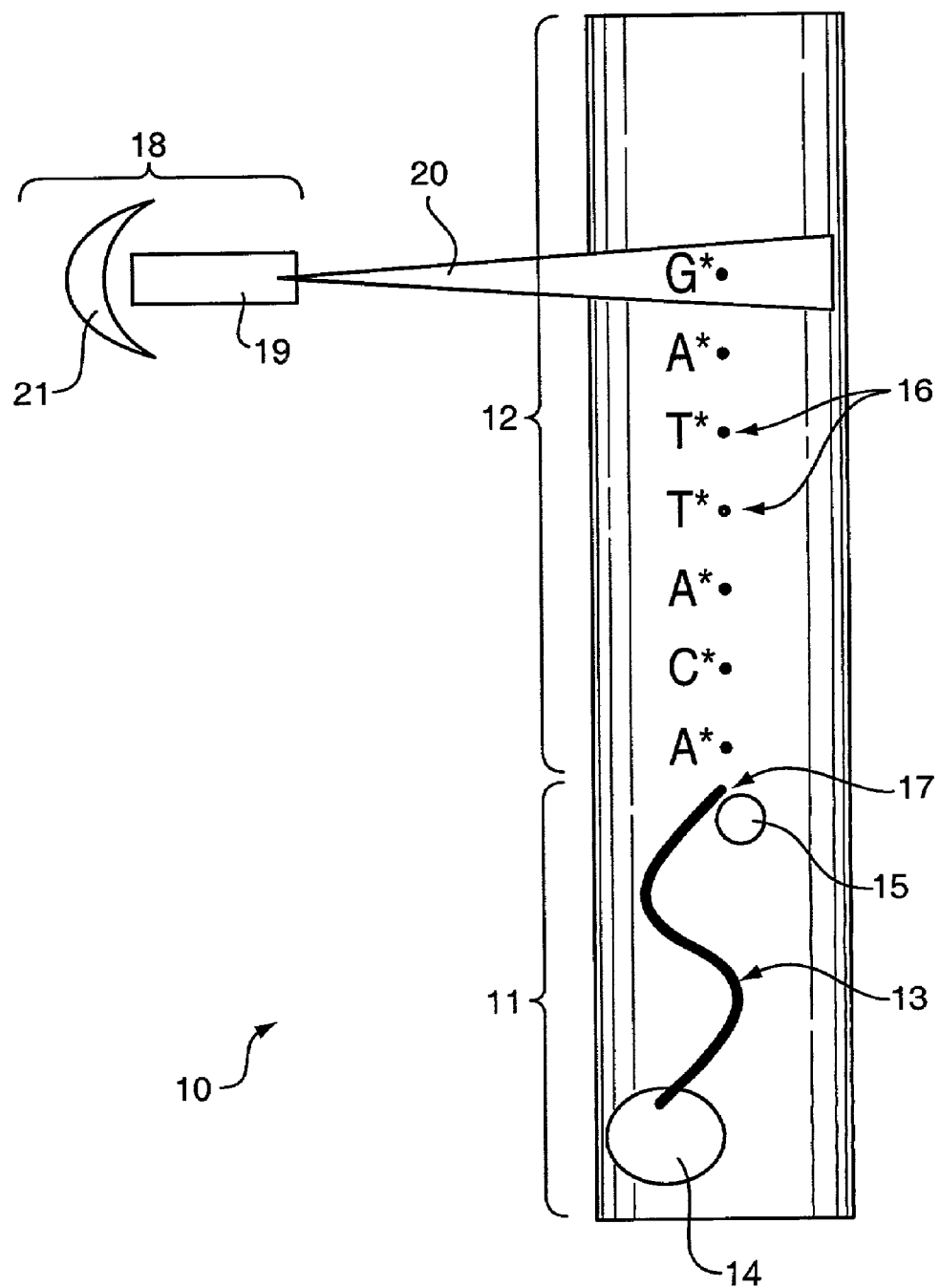
FIG. 1 illustrates an exemplary apparatus 10 (not to scale) and method for nucleic acid 13 sequencing, using nucleotides 16 covalently attached to Raman labels.

The disclosed methods and apparatus are of use for the rapid, automated sequencing of nucleic acids 13. In particular embodiments of the invention, the methods and apparatus 10, 100, 210 are suitable for obtaining the sequences of very long nucleic acid molecules 13 of greater than 1,000, greater than 2,000, greater than 5,000, greater than 10,000 greater than 20,000, greater than 50,000, greater than 100,000 or even more bases in length. Advantages over prior art methods include the ability to read long nucleic acid 13 sequences in a single sequencing run, greater speed of obtaining sequence data, decreased cost of sequencing and greater efficiency in operator time required per unit of sequence data.

In various embodiments of the invention, sequence information maybe obtained during the course of a single sequencing run, using a single nucleic acid molecule 13. In other embodiments of the invention, multiple copies of a nucleic acid molecule 13 may be sequenced in parallel or sequentially to confirm the nucleic acid sequence or to obtain complete sequence data. In alternative embodiments of the invention, both the nucleic acid molecule 13 and its complementary strand may be sequenced to confirm the accuracy of the sequence information.

In certain embodiments of the invention, the nucleic acid 13 to be sequenced is DNA, although it is contemplated that other nucleic acids 13 comprising RNA or synthetic nucleotide analogs could be sequenced as well. The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

In various embodiments of the invention, exemplified in FIG. 1, nucleotides may be covalently attached to Raman labels to enhance the Raman signal detected by surface enhanced Raman spectroscopy (SERS), surface enhanced resonance Raman spectroscopy (SERRS), coherent anti-Stokes Raman spectroscopy (CARS) or other known Raman detection techniques. In some embodiments of the invention, such labeled nucleotides may be incorporated into a newly synthesized nucleic acid strand 13 using standard nucleic acid polymerization techniques. Typically, either a primer of specific sequence or one or more random primers is allowed to hybridize to a template nucleic acid. Upon addition of a polymerase and labeled nucleotides, the Raman labeled nucleotides are covalently attached to the 3' end of the primer, resulting in the formation of a labeled nucleic acid strand 13 complementary in sequence to the template.

After synthesis, the labeled nucleic acid strand 13 may be digested with one or more exonucleases 15. The skilled artisan will realize that the disclosed methods are not limited to exonucleases 15 per se, but may utilize any enzyme or other reagent capable of sequentially removing nucleotides 16, 130 from at least one end of a nucleic acid 13. In certain embodiments of the invention, Raman labeled nucleotides 16, 130 are sequentially released from the 3' end 17 of the labeled nucleic acid 13. After separation from the labeled nucleic acid 13, the Raman labeled nucleotides 16, 130 are detected by a detection unit 18, 180, 300. Information on sequentially detected labeled nucleotides 16, 130 is used to compile a sequence of the labeled nucleic acid 13, which is complementary to the sequence of the template strand.

In some embodiments of the invention, the labeled nucleic acid strand 13 may be separated from the unlabeled template strand as well as unincorporated nucleotides prior to exonuclease 15 treatment. This may be accomplished, for example, by using a primer that has been cross-linked to a surface 14 or that contains biotin or a similar group that may be attached to a surface 14. Biotin labeled primers may be attached to a surface 14 that has been covalently modified with avidin or streptavidin. The labeled nucleic acid 13 may be separated from the unlabeled template strand by known techniques.

In certain embodiments of the invention, each of the four types of nucleotide may be attached to a distinguishable Raman label. In other embodiments of the invention, only the purine nucleotides (cytosine and/or thymine and/or uracil) may be labeled. In one exemplary embodiment, the labeled nucleotides may comprise biotin-labeled deoxycytidine-5'-triphosphate (biotin-dCTP) and digoxigenin-labeled deoxyuridine-5'-triphosphate(digoxigenin-dUTP).

Figure 2:
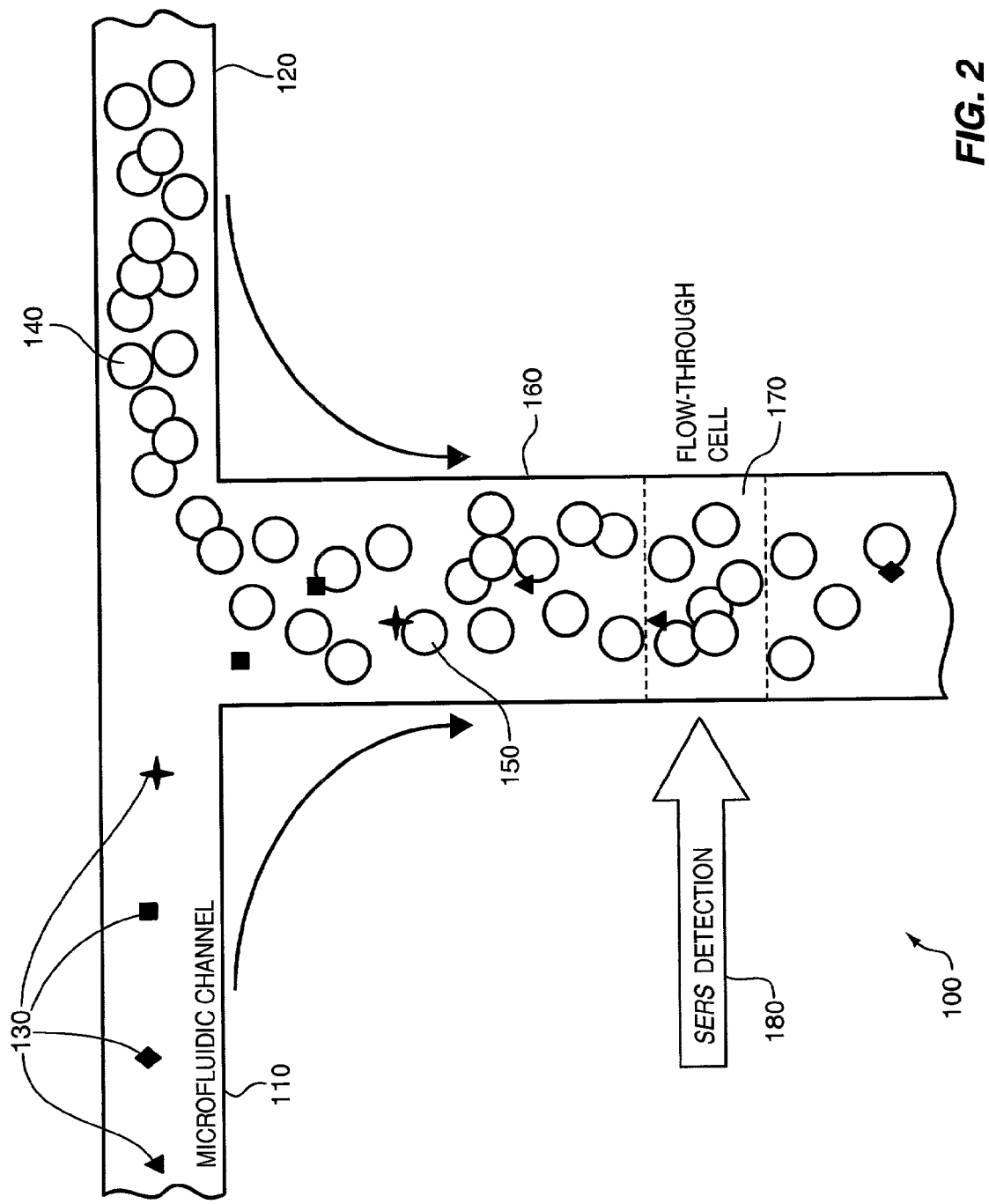
FIG. 2 illustrates an exemplary apparatus 100 (not to scale) and method for nucleic acid 13 sequencing in which the released nucleotides 130 are covalently attached to nanoparticles 140 prior to detection by surface enhance Raman spectroscopy (SERS) 180.

In alternative embodiments of the invention, exemplified in FIG. 2, the Raman signal may be enhanced by covalent attachment of nucleotides 16, 130 to nanoparticles 140. In certain embodiments of the invention, such attachment would follow exonuclease 15 treatment of a nucleic acid 13 as disclosed in FIG. 1. In some embodiments of the invention, the nanoparticles 140 are silver or gold, but other types of nanoparticles 140 known to provide surface enhanced Raman signals are contemplated. The nanoparticles 140 may either be single nanoparticles 140, aggregates of nanoparticles 140, or some mixture of single and aggregated nanoparticles 140. In certain embodiments of the invention, a linker compound may be used to attach the nucleotides 16, 130 to the nanoparticles 140. In various embodiments of the invention, the linker compound may be between 1 to 100 nanometers (nm), 2 to 90 nm, 3 to 80 nm, 4 to 70 nm, 5 to 60 nm, 10 to 50 nm, 15 to 40 nm or 20 to 30 nm in length. In certain embodiments of the invention, the linker compound may be between 1 to 50, 1 to 5, 2 to 10, 10 to 20 nm or about 5 nm in length. In other embodiments of the invention, two or more nanoparticles 140 may be attached together using linker compounds.

Following covalent attachment, the nanoparticle-nucleotide complexes 150 may pass through a flow-through cell 170, 290 where they are detected by SERS, SERRS and/or CARS using a detection unit 18, 180, 300. In some alternative embodiments of the invention, the nucleotides 16, 130 may be unmodified, while in other alternative embodiments the nucleotides 16, 130 may be modified with one or more Raman labels. In certain embodiments of the invention, each type of nucleotide 16, 130 may be attached to a distinguishable Raman label. In other embodiments only pyrimidines 16, 130 may be labeled.

Definitions

As used herein, "a" or "an" may mean one or more than one of an item.

As used herein, "operably coupled" means that there is a functional interaction between two or more units. For example, a detector 21, 310 may be "operably coupled" to a flow-through cell 170, 290 if the detector 21, 310 is arranged so that it may detect analytes, such as nucleotides 16, 130, as they pass through the flow-through cell 170, 290.

"Nucleic acid" 13 encompasses DNA, RNA, single-stranded, double-stranded or triple stranded and any chemical modifications thereof. Virtually any modification of the nucleic acid 13 is contemplated. As used herein, a single stranded nucleic acid 13 may be denoted by the prefix "ss", a double stranded nucleic acid 13 by the prefix "ds", and a triple stranded nucleic acid 13 by the prefix "ts."

A "nucleic acid" 13 may be of almost any length, from 10, 20, 30, 40, 50, 60, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule 13.

A "nucleoside" 16, 130 is a molecule comprising a purine or pyrimidine base (adenine—"A", cytosine—"C", guanine—"G", thymine—"T" or uracil—"U") or any chemical modification or structural analog thereof, covalently attached to a pentose sugar such as deoxyribose, ribose or derivatives or analogs of pentose sugars.

A "nucleotide" 16, 130 refers to a nucleoside 16, 130 further comprising at least one phosphate group covalently attached to the pentose sugar. In some embodiments of the invention, the nucleotides 16, 130 are ribonucleoside monophosphates 16, 130 or deoxyribonucleoside monophosphates 16, 130, although it is anticipated that nucleoside diphosphates or triphosphates 16, 130 could be produced and detected. In other embodiments of the invention, nucleosides 16, 130 may be released from the nucleic acid molecule 13. It is contemplated that various substitutions or modifications may be made in the structure of the nucleotides 16, 130, so long as they are capable of being incorporated into a nucleic acid 13 by polymerase activity and released by an exonuclease 15 or equivalent reagent. In embodiments of the invention involving one or more labels attached to one or more types of nucleotide 16, 130, the label may be attached to any portion of the nucleotide 16, 130, such as the base, the sugar or the phosphate groups or their analogs, so long as the label does not interfere with the polymerization and/or digestion of a nucleic acid 13. The terms "nucleotide" and "labeled nucleotide" encompass, but are not limited to, all non-naturally nucleotide complexes, such as nucleotide-nanoparticle complexes and nucleotide-label complexes.

A "Raman label" may be any organic or inorganic molecule, atom, complex or structure capable of producing a detectable Raman signal, including but not limited to synthetic molecules, dyes, naturally occurring pigments such as phycoerythrin, organic nanostructures such as C60, buckyballs and carbon nanotubes, metal nanostructures such as gold or silver nanoparticles or nanoprisms and nano-scale semiconductors such as quantum dots. Numerous examples of Raman labels are disclosed below. The skilled artisan will realize that such examples are not limiting, and that "Raman label" encompasses any organic or inorganic atom, molecule, compound or structure known in the art that can be detected by Raman spectroscopy.

Nucleic Acids

Nucleic acid molecules 13 to be sequenced may be prepared by any technique known in the art. In certain embodiments of the invention, the nucleic acids 13 are naturally occurring DNA or RNA molecules. Virtually any naturally occurring nucleic acid 13 may be prepared and sequenced by the disclosed methods including, without limit, chromosomal, mitochondrial and chloroplast DNA and ribosomal, transfer, heterogeneous nuclear and messenger RNA (mRNA). Methods for preparing and isolating various forms of nucleic acids 13 are known. (See, e.g.,

*Guide to Molecular Cloning Techniques*, eds. Berger and Kimmel, Academic Press, New York, N.Y., 1987; *Molecular Cloning: A Laboratory Manual,* 2nd Ed., eds. Sambrook, Fritsch and Maniatis, Cold Spring Harbor Press, Cold Spring Harbor, N.Y., 1989). The methods disclosed in the cited references are exemplary only and any variation known in the art may be used. In cases where single stranded DNA (ssDNA) 13 is to be sequenced, an ssDNA 13 may be prepared from double stranded DNA (dsDNA) by any known method. Such methods may involve heating dsDNA and allowing the strands to separate, or may alternatively involve preparation of ssDNA 13 from dsDNA by known amplification or replication methods, such as cloning into M13. Any such known method may be used to prepare ssDNA or ssRNA 13.

Although certain embodiments of the invention concern preparation of naturally occurring nucleic acids 13, virtually any type of nucleic acid 13 that can serve as a substrate for an exonuclease or equivalent reagent 15 could potentially be sequenced. For example, nucleic acids 13 prepared by various amplification techniques, such as polymerase chain reaction (PCR™) amplification, could be sequenced. (See U.S. Pat. Nos. 4,683,195, 4,683,202 and 4,800,159.) Nucleic acids 13 to be sequenced may alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts 13 may be isolated from vector DNA, for example, by excision with appropriate restriction endonucleases, followed by agarose gel electrophoresis. Methods for isolation of insert nucleic acids 13 are well known.

Isolation of Single Nucleic Acid Molecules

In certain embodiments of the invention, the nucleic acid molecule 13 to be sequenced is a single molecule of ssDNA or ssRNA. A variety of methods for selection and manipulation of single nucleic acid molecules 13 may be used, for example, hydrodynamic focusing, micromanipulator coupling, optical trapping, or a combination of these and similar methods. (See, e.g., Goodwin et al., 1996, *Acc. Chem. Res.* 29:607–619; U.S. Pat. Nos. 4,962,037; 5,405,747; 5,776,674; 6,136,543; 6,225,068.)

In certain embodiments of the invention, microfluidics or nanofluidics may be used to sort and isolate nucleic acid molecules 13. Hydrodynamics may be used to manipulate the movement of nucleic acids 13 into a microchannel, microcapillary, or a micropore. In one embodiment of the invention, hydrodynamic forces may be used to move nucleic acid molecules 13 across a comb structure to separate single nucleic acid molecules 13. Once the nucleic acid molecules 13 have been separated, hydrodynamic focusing may be used to position the molecules 13 within a reaction chamber 11, 220. A thermal or electric potential, pressure or vacuum can also be used to provide a motive force for manipulation of nucleic acids 13. In exemplary embodiments of the invention, manipulation of nucleic acids 13 for sequencing may involve the use of a channel block design incorporating microfabricated channels and an integrated gel material (see U.S. Pat. Nos. 5,867,266 and 6,214,246).

In another embodiment of the invention, a sample containing the nucleic acid molecule 13 may be diluted prior to coupling to an immobilization surface 14. In exemplary embodiments of the invention, the immobilization surface 14 may be in the form of magnetic or non-magnetic beads or other discrete structural units. At an appropriate dilution, each bead 14 will have a statistical probability of binding zero or one nucleic acid molecule 13. Beads 14 with one attached nucleic acid molecule 13 may be identified using, for example, fluorescent dyes and flow cytometer sorting or magnetic sorting. Depending on the relative sizes and uniformity of the beads 14 and the nucleic acids 13, it may be possible to use a magnetic filter and mass separation to separate beads 14 containing a single bound nucleic acid molecule 13. In other embodiments of the invention, multiple nucleic acids 13 attached to a single bead or other immobilization surface 14 may be sequenced.

In alternative embodiments of the invention, a coated fiber tip 14 may be used to generate single molecule nucleic acids 13 for sequencing (e.g., U.S. Pat. No. 6,225,068). In other alternative embodiments, the immobilization surfaces 14 may be prepared to contain a single molecule of avidin or other cross-linking agent. Such a surface 14 could attach a single biotinylated nucleic acid molecule 13 to be sequenced. This embodiment is not limited to the avidin-biotin binding system, but may be adapted to any known coupling system.

In other alternative embodiments of the invention, an optical trap may be used for manipulation of single molecule nucleic acid molecules 13 for sequencing. (E.g., U.S. Pat. No. 5,776,674). Exemplary optical trapping systems are commercially available from Cell Robotics, Inc. (Albuquerque, N.Mex.), S+L GmbH (Heidelberg, Germany) and P.A.L.M. Gmbh (Wolfratshausen, Germany).

Raman Labels

Certain embodiments of the invention may involve attaching a label to the nucleotides 16, 130 to facilitate their measurement by the detection unit 18, 180, 300. Non-limiting examples of labels that could be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins and aminoacridine. These and other Raman labels may be obtained from commercial sources (e.g., Molecular Probes, Eugene, Oreg.).

Polycyclic aromatic compounds may function as Raman labels, as is known in the art. Other labels that may be of use for particular embodiments of the invention include cyanide, thiol, chlorine, bromine, methyl, phosphorus and sulfur. In certain embodiments of the invention, carbon nanotubes may be of use as Raman labels. The use of labels in Raman spectroscopy is known (e.g., U.S. Pat. Nos. 5,306,403 and 6,174,677). The skilled artisan will realize that the Raman labels used should generate distinguishable Raman spectra and may be specifically bound to or associated with different types of nucleotides 16, 130.

Labels may be attached directly to the nucleotides 16, 130 or may be attached via various linker compounds. Cross-linking reagents and linker compounds of use in the disclosed methods are further described below. Alternatively, nucleotides that are covalently attached to Raman labels are available from standard commercial sources (e.g., Roche Molecular Biochemicals, Indianapolis, Ind.; Promega Corp., Madison, Wis.; Ambion, Inc., Austin, Tex.; Amersham Pharmacia Biotech, Piscataway, N.J.). Raman labels that contain reactive groups designed to covalently react with other molecules, such as nucleotides 16, 130, are commercially available (e.g., Molecular Probes, Eugene, Oreg.). Methods for preparing labeled nucleotides and incorporating them into nucleic acids 13 are known (e.g., U.S. Pat. Nos. 4,962,037; 5,405,747; 6,136,543; 6,210,896).

Nanoparticles

Certain embodiments of the invention involve the use of nanoparticles 140 to enhance the Raman signal obtained from nucleotides 16, 130. In some embodiments of the invention, the nanoparticles 140 are silver or gold nanoparticles 140, although any nanoparticles 140 capable of providing a surface enhanced Raman spectroscopy (SERS) signal may be used. In alternative embodiments of the invention, the nanoparticles 140 may be nanoprisms (Jin et al., Science 294:1902–3, 2001.) In various embodiments of the invention, nanoparticles 140 of between 1 nm and 2 micrometers ($\mu$m) in diameter may be used. In alternative embodiments of the invention, nanoparticles 140 of between 2 nm to 1 $\mu$m, 5 nm to 500 nm, 10 nm to 200 nm, 20 nm to 100 nm, 30 nm to 80 nm, 40 nm to 70 nm or 50 to 60 nm diameter are contemplated. In certain embodiments of the invention, nanoparticles 140 with an average diameter of 10 to 50 nm, 50 to 100 nm or about 100 nm are contemplated. The nanoparticles 140 may be approximately spherical, rod-like, edgy, faceted or pointy in shape, although nanoparticles 140 of any shape or of irregular shape may be used. Methods of preparing nanoparticles are known (e.g., U.S. Pat. Nos. 6,054,495; 6,127,120; 6,149,868; Lee and Meisel, J. Phys. Chem. 86:3391–3395, 1982; Jin et al., 2001). Nanoparticles may also be obtained from commercial sources (e.g., Nanoprobes Inc., Yaphank, N.Y.; Polysciences, Inc., Warrington, Pa.).

In certain embodiments of the invention, the nanoparticles 140 may be single nanoparticles 140 and/or random aggregates of nanoparticles 140 (colloidal nanoparticles 140). In other embodiments of the invention, nanoparticles 140 may be cross-linked to produce particular aggregates of nanoparticles 140, such as dimers, trimers, tetramers or other aggregates. Certain alternative embodiments of the invention may use heterogeneous mixtures of aggregates of different size, while other alternative embodiments may use homogenous populations of nanoparticles 140. In certain embodiments of the invention, aggregates containing a selected number of nanoparticles 140 (dimers, trimers, etc.) may be enriched or purified by known techniques, such as ultracentrifugation in sucrose solutions. In various embodiments of the invention, nanoparticle 140 aggregates of about 100, 200, 300, 400, 500, 600, 700, 800, 900 to 1000 nm in size or larger are contemplated.

Methods of cross-linking nanoparticles 140 are known (e.g., Feldheim, "Assembly of metal nanoparticle arrays using molecular bridges," The Electrochemical Society Interface, Fall, 2001, pp. 22–25). Gold nanoparticles 140 may be cross-linked, for example, using bifunctional linker compounds bearing terminal thiol or sulfhydryl groups. Upon reaction with gold nanoparticles 140, the linker forms nanoparticle 140 dimers that are separated by the length of the linker. In other embodiments of the invention, linkers with three, four or more thiol groups may be used to simultaneously attach to multiple nanoparticles 140 (Feldheim, 2001). The use of an excess of nanoparticles 140 to linker compounds prevents formation of multiple cross-links and nanoparticle 140 precipitation. Aggregates of silver nanoparticles 140 may be formed by standard synthesis methods known in the art.

In alternative embodiments of the invention, the nanoparticles 140 may be modified to contain various reactive groups before they are attached to linker compounds. Modified nanoparticles 140 are commercially available, such as Nanogold® nanoparticles 140 from Nanoprobes, Inc. (Yaphank, N.Y.). Nanogold® nanoparticles 140 may be obtained with either single or multiple maleimide, amine or other groups attached per nanoparticle 140. The Nanogold® nanoparticles 140 are also available in either positively or negatively charged form. Such modified nanoparticles 140 may be attached to a variety of known linker compounds to provide dimers, trimers or other aggregates of nanoparticles 140.

The type of linker compound used is not limiting, so long as it results in the production of small aggregates of nanoparticles 140 that will not precipitate in solution. In some embodiments of the invention, the linker group may comprise phenylacetylene polymers (Feldheim, 2001). Alternatively, linker groups may comprise polytetrafluoroethylene, polyvinyl pyrrolidone, polystyrene, polypropylene, polyacrylamide, polyethylene or other known polymers. The linker compounds of use are not limited to polymers, but may also include other types of molecules such as silanes, alkanes, derivatized silanes or derivatized alkanes.

In various embodiments of the invention, the nanoparticles 140 may be covalently attached to nucleotides 16, 130. In alternative embodiments of the invention, the nucleotides 16, 130 may be directly attached to the nanoparticles 140, or may be attached to linker compounds that are covalently or non-covalently bonded to the nanoparticles 140. In such embodiments of the invention, rather than cross-inking two or more nanoparticles 140 together the linker compounds may be used to attach a nucleotide 16, 130 to a nanoparticle 140 or a nanoparticle 140 aggregate. In particular embodiments of the invention, the nanoparticles 140 may be coated with derivatized silanes. Such modified silanes may be covalently attached to nucleotides 16, 130 using standard methods. Various methods known for cross-linking nucleic acids 13 to surfaces 14 discussed below may also be used to attach nucleotides 16, 130 to nanoparticles 140. It is contemplated that the linker compounds used to attach nucleotides 16, 130 may be of almost any length, ranging from about 0.05, 0.1, 0.2, 0.5, 0.75, 1, 2, 3, 4, 5, 6, 7, 8, 9, 10, 11, 12, 13, 14, 15, 16, 17, 18, 19, 20, 21, 22, 23, 24, 25, 27, 30, 35, 40, 45, 50, 55, 60, 65, 60, 80, 90 to 100 nm or even greater length. Certain embodiments of the invention may use linkers of heterogeneous length.

In other embodiments of the invention, nucleotides 16, 130 may be adsorbed on the surface of the nanoparticles 140 or may be in close proximity to the nanoparticles 140 (between about 0.2 and 1.0 nm). The skilled artisan will realize that it covalent attachment of the nucleotides 16, 130 to nanoparticles 140 is not required in order to generate an enhanced Raman signal by SERS, SERRS or CARS.

In the exemplary embodiment of the invention disclosed in FIG. 2, the nucleotides 130 are attached to nanoparticles 140 as they travel down a microfluidic channel 160 to form nucleotide-nanoparticle complexes 150. In certain embodiments of the invention, the length of time available for the cross-linking reaction to occur may be very limited. Such embodiments may utilize highly reactive cross-linking groups with rapid reaction rates, such as epoxide groups, azido groups, arylazido groups, triazine groups or diazo groups. In certain embodiments of the invention, the cross-linking groups may be photoactivated by exposure to intense light, such as a laser. For example, photoactivation of diazo or azido compounds results in the formation, respectively, of highly reactive carbene and nitrene moieties. In certain embodiments of the invention, the reactive groups may be selected so that they can only attach the nanoparticles 140 to nucleotides 16, 130, rather than cross-linking the nanoparticles 140 to each other. The selection and preparation of reactive cross-linking groups capable of binding to nucleotides 16, 130 is known in the art. In alternative embodiments of the invention, nucleotides 16, 130 may themselves be covalently modified, for example with a sulfhydryl group that can attach to gold nanoparticles 140.

In certain embodiments of the invention, nanoparticles 140 may be manipulated into microfluidic channels 120, 160, 270, 280 by any method known in the art, such as microfluidics, nanofluidics, hydrodynamic focusing or electro-osmosis. In some embodiments of the invention, use of charged linker compounds or charged nanoparticles 140 may facilitate manipulation of nanoparticles 140 through the use of electrical gradients.

Immobilization of Nucleic Acids

In certain embodiments of the invention, as exemplified in FIG. 1, one or more nucleic acid molecules 13 may be attached to a surface 14 such as functionalized glass, silicon, silicate, PDMS (polydimethyl siloxane), polyvinylidene difluoride (PVDF), silver or other metal coated surfaces, quartz, plastic, PTFE (polytetrafluoroethylene), PVP (polyvinyl pyrrolidone), poly(vinyl chloride), poly(methyl methacrylate), poly(dimethyl siloxane), polystyrene, polypropylene, polyacrylamide, latex, nylon, nitrocellulose, glass beads, magnetic beads, photopolymers which contain photoreactive species such as nitrenes, carbenes and ketyl radicals capable of forming covalent links with nucleic acid molecules 13 (See U.S. Pat. Nos. 5,405,766 and 5,986,076) or any other material known in the art that is capable of having functional groups such as amino, carboxyl, thiol, hydroxyl or Diels-Alder reactants incorporated on its surface 14.

In some embodiments of the invention, the surface functional groups may be covalently attached to cross-linking compounds so that binding interactions between nucleic acid molecule 13 and exonuclease 15 and/or polymerase may occur without steric hindrance. Typical cross-linking groups include ethylene glycol oligomers and diamines. Attachment may be by either covalent or non-covalent binding. Various methods of attaching nucleic acid molecules 13 to surfaces 14 are known in the art and may be employed. In certain embodiments of the invention, the nucleic acid molecule 13 is fixed in place and immersed in a microfluidic flow down a flow path 12 and/or microfluidic channel 110, 160, 260, 280 that transports the released nucleotides 16, 130 past a detection unit 18, 180, 300. In non-limiting examples, the microfluidic flow may result from a bulk flow of solvent down a flow path 12 and/or microfluidic channel 110, 160, 260, 280.

In alternative embodiments of the invention, the bulk medium moves only slowly or not at all, but charged species within the solution (such as negatively charged nucleotides 16, 130) move down a flow path 12 and/or microfluidic channel 110, 160, 260, 280 in response to an externally applied electrical field.

Immobilization of nucleic acid molecules 13 may be achieved by a variety of known methods. In an exemplary embodiment of the invention, immobilization may be achieved by coating a surface 14 with streptavidin or avidin and the subsequent attachment of a biotinylated nucleic acid 13 (Holmstrom et al, Anal. Biochem. 209:278–283, 1993). Immobilization may also occur by coating a silicon, glass or other surface 14 with poly-L-Lys (lysine) or poly L-Lys, Phe (phenylalanine), followed by covalent attachment of either amino- or sulfhydryl-modified nucleic acids 13 using bifunctional crosslinking reagents (Running et al., BioTechniques 8:276–277, 1990; Newton et al., Nucleic Acids Res. 21:1155–62, 1993). Amine residues may be coated on a surface 14 through the use of aminosilane.

Immobilization may take place by direct covalent attachment of 5'-phosphorylated nucleic acids 13 to chemically modified surfaces 14 (Rasmussen et al., Anal. Biochem. 198:138–142, 1991). The covalent bond between the nucleic acid 13 and the surface 14 may be formed by condensation with a water-soluble carbodiimide. This method facilitates a predominantly 5'-attachment of the nucleic acids 13 via their 5'-phosphates.

DNA 13 is commonly bound to glass by first silanizing the glass surface 14, then activating with carbodiimide or glutaraldehyde. Alternative procedures may use reagents such as 3-glycidoxypropyltrimethoxysilane (GOP) or aminopropyltrimethoxysilane (APTS) with DNA 13 linked via amino linkers incorporated at either the 3' or 5' end of the molecule. DNA 13 may be bound directly to membrane surfaces 14 using ultraviolet radiation. Other non-limiting examples of immobilization techniques for nucleic acids 13 are disclosed in U.S. Pat. Nos. 5,610,287, 5,776,674 and 6,225,068.

Bifunctional cross-linking reagents may be of use in various embodiments of the invention, such as attaching a nucleic acid molecule 13 to a surface 14. The bifunctional cross-linking reagents can be divided according to the specificity of their functional groups, e.g., amino, guanidino, indole, or carboxyl specific groups. Exemplary methods for cross-linking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl)carbodiimide (EDC).

Nucleic Acid Synthesis

Polymerases

Certain embodiments of the invention involve binding of a synthetic reagent, such as a DNA polymerase, to a primer molecule and the addition of Raman labeled nucleotides to the 3' end of the primer. Non-limiting examples of polymerases include DNA polymerases, RNA polymerases, reverse transcriptases, and RNA-dependent RNA polymerases. The differences between these polymerases in terms of their "proofreading" activity and requirement or lack of requirement for primers and promoter sequences are known in the art. Where RNA polymerases are used as the polymerase, a template molecule to be sequenced may be double-stranded DNA. Non-limiting examples of polymerases include *Thermatoga maritima* DNA polymerase, AmplitaqFS™ DNA polymerase, Taquenase™ DNA polymerase, ThermoSequenase™, Taq DNA polymerase, Qbeta™ replicase, T4 DNA polymerase, *Thermus thermophilus* DNA polymerase, RNA-dependent RNA polymerase and SP6 RNA polymerase.

A number of polymerases are commercially available, including Pwo DNA Polymerase (Boehringer Mannheim Biochemicals, Indianapolis, Ind.); Bst Polymerase (Bio-Rad Laboratories, Hercules, Calif.); IsoTherm™ DNA Polymerase (Epicentre Technologies, Madison, Wis.); Moloney Murine Leukemia Virus Reverse Transcriptase, Pfu DNA Polymerase, Avian Myeloblastosis Virus Reverse Transcriptase, *Thermus flavus* (Tfl) DNA Polymerase and *Thermococcus litoralis* (Tli) DNA Polymerase (Promega Corp., Madison, Wis.); RAV2 Reverse Transcriptase, HIV-1 Reverse Transcriptase, T7 RNA Polymerase, T3 RNA Polymerase, SP6 RNA Polymerase, *E. coli* RNA Polymerase, *Thermus aquaticus* DNA Polymerase, T7 DNA Polymerase +/−3'→5' exonuclease, Klenow Fragment of DNA Polymerase I, Thermus 'ubiquitous' DNA Polymerase, and DNA polymerase I (Amersham Pharmacia Biotech, Piscataway, N.J.). Any polymerase known in the art capable of template dependent polymerization of labeled nucleotides may be used. (See, e.g., Goodman and Tippin, Nat. Rev. Mol. Cell Biol. 1(2):101–9, 2000; U.S. Pat. No. 6,090,589.) Methods of using polymerases to synthesize nucleic acids 13 from labeled nucleotides are known (e.g., U.S. Pat. Nos. 4,962,037; 5,405,747; 6,136,543; 6,210,896).

Primers

Generally, primers are between ten and twenty bases in length, although longer primers may be employed. In certain embodiments of the invention, primers are designed to be complementary in sequence to a known portion of a template nucleic acid molecule. Known primer sequences may be used, for example, where primers are selected for identifying sequence variants adjacent to known constant chromosomal sequences, where an unknown nucleic acid sequence is inserted into a vector of known sequence, or where a native nucleic acid has been partially sequenced. Methods for synthesis of primers of any sequence are known. Other embodiments of the invention involve sequencing a nucleic acid 13 in the absence of a known primer-binding site. In such cases, it may be possible to use random primers, such as random hexamers or random oligomers to initiate polymerization.

Nucleic Acid Digestion

In certain embodiments of the invention, exemplified in FIG. 1, methods of nucleic acid 13 sequencing involve binding of an exonuclease 15 or equivalent reagent to the free end 17 of a nucleic acid molecule 13 and removal of nucleotides 16, 130 one at a time. Non-limiting examples of nucleic acid digesting enzymes 15 of potential use include *E. coli* exonuclease I, III, V or VII, Bal 31 exonuclease, mung bean nuclease, S1 nuclease, *E. coli* DNA polymerase I holoenzyme or Klenow fragment, RecJ, exonuclease T, T4 or T7 DNA polymerase, Taq polymerase, exonuclease T7 gene 6, snake venom phosphodiesterase, spleen phosphodiesterase, *Thermococcus litoralis* DNA polymerase, Pyrococcus sp. GB-D DNA polymerase, lambda exonuclease, *S. aureus* micrococcal nuclease, DNase I, ribonuclease A, T1 micrococcal nuclease, or other exonucleases known in the art. Exonucleases 15 are available from commercial sources such as New England Biolabs (Beverly, Mass.), Amersham Pharmacia Biotech (Piscataway, N.J.), Promega (Madison, Wis.), Sigma Chemicals (St. Louis, Mo.) or Boehringer Mannheim (Indianapolis, Ind.).

The skilled artisan will realize that enzymes with exonuclease 15 activity may remove nucleotides 16, 130 from the 5' end, the 3' end, or either end of nucleic acid molecules 13. They can show specificity for RNA, DNA or both RNA and DNA 13. Their activity may depend on the use of either single or double-stranded nucleic acids 13. They may be differentially affected by salt concentration, temperature, pH, or divalent cations. These and other properties of exonucleases 15 are known in the art. In certain embodiments of the invention, the rate of exonuclease 15 activity may be manipulated to coincide with the optimal rate of analysis of nucleotides 16, 130 by the detection unit 18, 180, 300. Various methods are known for adjusting the rate of exonuclease 15 activity, including adjusting the temperature, pressure, pH, salt or divalent cation concentration in a reaction chamber 11, 220.

Although nucleoside monophosphates 16, 130 will generally be released from nucleic acids 13 by exonuclease 15 activity, the embodiments of the invention are not limited to detection of any particular form of free nucleotide or nucleoside 16, 130 but encompass any monomer 16, 130 that may be released from a nucleic acid 13.

Reaction Chamber and Integrated Chip

As exemplified in FIG. 1, some embodiments of the invention concern apparatus 10, 100, 210 comprising a reaction chamber 11, 220 designed to contain an immobilization surface 14, nucleic acid molecule 13, exonuclease 15 and nucleotides 16, 130 in an aqueous environment. In some embodiments of the invention, the reaction chamber 11, 220 may be temperature controlled, for example by incorporation of Pelletier elements or other methods known in the art. Methods of controlling temperature for low volume liquids are known. (See, e.g., U.S. Pat. Nos. 5,038,853, 5,919,622, 6,054,263 and 6,180,372.)

In certain embodiments of the invention, the reaction chamber 11, 220 and any associated fluid channels, for example, a flow path 12, microfluidic channels 110, 160, 260, 280 or channels 120, 230, 240, 270, 350, 360 to provide connections to waste ports, to a nucleic acid 13 loading port, to a nanoparticle reservoir 370, to a source of exonuclease 15 or other fluid compartments are manufactured in a batch fabrication process, as known in the fields of computer chip manufacture and/or microcapillary chip manufacture. In some embodiments of the invention, the reaction chamber 11, 220 and other components of the apparatus 10, 100, 210, such as the flow path 12 and/or microfluidic channels 120, 160, 260, 280 may be manufactured as a single integrated chip. Such a chip may be manufactured by methods known in the art, such as by photolithography and etching. However, the manufacturing method is not limiting and other methods known in the art may be used, such as laser ablation, injection molding, casting, molecular beam epitaxy, dip-pen nanolithograpy, chemical vapor deposition (CVD) fabrication, electron beam or focused ion beam technology or imprinting techniques. Methods for manufacture of nanoelectromechanical systems may be used for certain embodiments of the invention. (See, e.g., Craighead, Science 290:1532–36, 2000.) Microfabricated chips are commercially available from, e.g., Caliper Technologies Inc. (Mountain View, Calif.) and ACLARA BioSciences Inc. (Mountain View, Calif.).

To facilitate detection of nucleotides 16, 130 by the detection unit 18, 180, 300 the material comprising the flow path 12 or flow-through cell 170, 290 may be selected to be transparent to electromagnetic radiation at the excitation and emission frequencies used for the detection unit 18, 180, 300. Glass, silicon, and any other materials that are generally transparent in the wavelengths used for Raman spectroscopy may be used. In some embodiments of the invention the surfaces of the flow path 12 or flow-through cell 170, 290 that are opposite the detection unit 18, 180, 300 may be coated with silver, gold, platinum, copper, aluminum or other materials that are relatively opaque to the detection unit 18, 180, 300. In that position, the opaque material is available to enhance the Raman signal, for example by SERS, while not interfering with the function of the detection unit 18, 180, 300. Alternatively, the flow path 12 or flow-through cell 170, 290 may contain a mesh comprising silver, gold, platinum, copper, aluminum or other Raman signal enhancing metal.

Flow Path and Microfluidic Channels

In certain embodiments of the invention, the nucleotides 16, 130 released from a nucleic acid 13 are moved down a flow path 12 and/or microfluidic channels 110, 160, 260, 280 past a detection unit 18, 180, 300. A non-limiting example of techniques for transport of nucleotides 16, 130 includes microfluidic techniques. The flow path 12 and/or microfluidic channels 110, 160, 260, 280 can comprise a microcapillary (e.g. from ACLARA BioSciences Inc., Mountain View, Calif.) or a liquid integrated circuit (e.g., Caliper Technologies Inc., Mountain View, Calif.).

In certain embodiments of the invention, the nucleotides 16, 130 to be detected move down the flow path 12 and/or microfluidic channels 110, 160, 260, 280 by bulk flow of solvent. In other embodiments of the invention, microcapillary electrophoresis may be used to transport nucleotides 16, 130 down the flow path 12 and/or microfluidic channels 110, 160, 260, 280. Microcapillary electrophoresis generally involves the use of a thin capillary or channel that may or may not be filled with a particular separation medium. Electrophoresis of appropriately charged molecular species, such as negatively charged nucleotides 16, 130, occurs in response to an imposed electrical field, negative on the reaction chamber 11, 220 side of the apparatus 10, 100, 210 and positive on the detection unit 18, 180, 300 side. Although electrophoresis is often used for size separation of a mixture of components that are simultaneously added to the microcapillary, it can also be used to transport similarly sized nucleotides 16, 130 that are sequentially released from a nucleic acid 13. Because the purine nucleotides (A, G) 16, 130 are larger than the pyrimidine nucleotides (C, T, U) 16, 130 and would therefore migrate more slowly, the length of the flow path 12 and/or microfluidic channels 110, 160, 260, 280 and the corresponding transit time past the detection unit 18, 180, 300 may kept to a minimum to prevent differential migration from mixing up the order of nucleotides 16, 130 released from the nucleic acid 13. Alternatively, the medium filling the microcapillary may be selected so that the migration rates of purine and pyrimidine nucleotides 16, 130 down the flow path 12 and/or microfluidic channels 110, 160, 260, 280 are similar or identical. Methods of microcapillary electrophoresis have been disclosed, for example, by Woolley and Mathies (*Proc. Natl. Acad. Sci. USA* 91:11348–352, 1994).

In certain embodiments of the invention, flow paths 12 and/or microfluidic channels 110, 160, 260, 280 may contain aqueous solutions with relatively high viscosity, such as glycerol solutions. Such high viscosity solutions may serve to decrease the flow rate and increase the reaction time available, for example, for cross-linking nucleotides 16, 130 to nanoparticles 140.

Microfabrication of microfluidic devices, including microcapillary electrophoretic devices has been disclosed in, e.g., Jacobsen et al. (*Anal.*Biochem, 209:278–283,1994); Effenhauser et al. (*Anal. Chem.* 66:2949–2953, 1994); Harrison et al. (Science 261:895–897, 1993) and U.S. Pat. No. 5,904,824. These methods may comprise micromolding techniques with silicon masters made using standard photolithography or focused ion beam techniques, or photolithographic etching of micron scale channels on silica, silicon or other crystalline substrates or chips. Such techniques may be readily adapted for use in the disclosed methods and apparatus. In some embodiments of the invention, the microcapillary may be fabricated from the same materials used for fabrication of a reaction chamber 11, 220, using techniques known in the art.

Detection Unit

In various embodiments of the invention, the detection unit 18, 180, 300 is designed to detect and quantify nucleotides 16, 130 by Raman spectroscopy. Methods for detection of nucleotides 16, 130 by Raman spectroscopy are known in the art. (See, e.g., U.S. Pat. Nos. 5,306,403; 6,002,471; 6,174,677). Variations on surface enhanced Raman spectroscopy (SERS), surface enhanced resonance Raman spectroscopy (SERRS) and coherent anti-Stokes Raman spectroscopy (CARS).have been disclosed. The sensitivity of Raman detection is enhanced by a factor of $10^6$ or more for molecules adjacent to roughened metal surfaces, such as silver, gold, platinum, copper or aluminum surfaces.

A non-limiting example of a Raman detection unit 18, 180, 300 is disclosed in U.S. Pat. No. 6,002,471. An excitation beam 20, 330 is generated by either a frequency doubled Nd:YAG laser 19, 320 at 532 nm wavelength or a frequency doubled Ti:sapphire laser 19, 320 at 365 nm wavelength. Pulsed laser beams 20, 330 or continuous laser beams 20, 330 may be used. The excitation beam 20, 330 passes through confocal optics and a microscope objective, and is focused onto the flow path 12 and/or the flow-through cell 170, 290. The Raman emission light from the nucleotides 16, 130 is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector 21, 310, comprising an avalanche photodiode interfaced with a computer for counting and digitization of the signal.

Another example of a Raman detection unit 18, 180, 300 is disclosed in U.S. Pat. No. 5,306,403, including a Spex Model 1403 double-grating spectrophotometer 21, 310 with a gallium-arsenide photomultiplier tube (RCA Model C31034 or Burle Industries Model C3103402) operated in the single-photon counting mode. The excitation source 19, 320 comprises a 514.5 nm line argon-ion laser 19, 320 from SpectraPhysics, Model 166, and a 647.1 nm line of a krypton-ion laser 19, 320 (Innova 70, Coherent).

Alternative excitation sources 19, 320 include a nitrogen laser 19, 320 (Laser Science Inc.) at 337 nm and a helium-cadmium laser 19, 320 (Liconox) at 325 nm (U.S. Pat. No. 6,174,677), a light emitting diode 19, 320, an Nd:YLF laser 19, 320, and/or various ions lasers 19, 320 and/or dye lasers 19, 320. The excitation beam 20, 330 may be spectrally purified with a bandpass filter (Corion) and may be focused on the flow path 12 and/or flow-through cell 170, 290 using a 6× objective lens (Newport, Model L6X). The objective lens may be used to both excite the nucleotides 16, 130 and to collect the Raman signal, by using a holographic beam splitter (Kaiser Optical Systems, Inc., Model HB 647-26N18) to produce a right-angle geometry for the excitation beam 20, 330 and the emitted Raman signal. A holographic notch filter (Kaiser Optical Systems, Inc.) may be used to reduce Rayleigh scattered radiation. Alternative Raman detectors 21, 310 include an ISA HR-320 spectrograph equipped with a red-enhanced intensified charge-coupled device (RE-ICCD) detection system (Princeton Instruments). Other types of detectors 21, 310 may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection of nucleotides 16, 130, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Information Processing and Control System and Data Analysis

In certain embodiments of the invention, the nucleic acid sequencing apparatus 10, 100, 210 may comprise an information processing system. The disclosed methods and apparatus 10, 100, 210 are not limiting for the type of information processing system used. An exemplary information processing system may incorporate a computer comprising a bus for communicating information and a processor for processing information. In one embodiment of the invention, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, or a Pentium Xeon® processor (Intel Corp., Santa Clara, Calif.). In various other embodiments of the invention, the processor may be based on Intel® architecture, such as Intel® IA-32 or Intel® IA-64 architecture. Alternatively, other processors may be used. The information processing and control system may further comprise any peripheral devices known in the art, such as memory, display, keyboard and/or other devices.

In particular embodiments of the invention, the detection unit 18, 180, 300 may be operably coupled to the information processing system. Data from the detection unit 18, 180, 300 may be processed by the processor and data stored in memory. Data on emission profiles for standard nucleotides 16, 130 may also be stored in memory. The processor may compare the emission spectra from nucleotides 16, 130 in the flow path 12 and/or flow-through cell 170, 290 to identify the type of nucleotide 16, 130 released from the nucleic acid molecule 13. The memory may also store the sequence of nucleotides 16, 130 released from the nucleic acid molecule 13. The processor may analyze the data from the detection unit 18, 180, 300 to determine the sequence of the nucleic acid 13. The information processing system may also perform standard procedures such as subtraction of background signals and "base-calling" determination when overlapping signals are detected.

While the disclosed methods may be performed under the control of a programmed processor, in alternative embodiments of the invention, the methods may be fully or partially implemented by any programmable or hardcoded logic, such as Field Programmable Gate Arrays (FPGAs), TTL logic, or Application Specific Integrated Circuits (ASICs). Additionally, the disclosed methods may be performed by any combination of programmed general purpose computer components and/or custom hardware components.

Following the data gathering operation, the data will typically be reported to a data analysis operation. To facilitate the analysis operation, the data obtained by the detection unit 18, 180, 300 will typically be analyzed using a digital computer such as that described above. Typically, the computer will be appropriately programmed for receipt and storage of the data from the detection unit 18, 180, 300 as well as for analysis and reporting of the data gathered.

In certain embodiments of the invention, custom designed software packages may be used to analyze the data obtained from the detection unit 18, 180, 300. In alternative embodiments of the invention, data analysis may be performed, using an information processing system and publicly available software packages. Non-limiting examples of available software for DNA sequence analysis include the PRISM™ DNA Sequencing Analysis Software (Applied Biosystems, Foster City, Calif.), the Sequencher™ package (Gene Codes, Ann Arbor, Mich.), and a variety of software packages available through the National Biotechnology Information Facility at website www.nbif.org/links/1.4.1.php.

EXAMPLES

Example 1

Nucleic Acid Sequencing Using Raman Labeled Nucleotides

Certain embodiments of the invention, exemplified in FIG. 1, involve sequencing of individual single-stranded nucleic acid molecules 13 that are attached to an immobilization surface 14 in a reaction chamber 11, 220 and disassembled in a deconstruction reaction. In such embodiments of the invention, the reaction chamber 11, 220 contains one or more exonucleases 15 that sequentially remove one nucleotide 16, 130 at a time from the unattached end 17 of the nucleic acid molecule 13.

As the nucleotides 16, 130 are released, they move down a flow path 12 past a detection unit 18, 180, 300. The detection unit 18, 180, 300 comprises an excitation source 19, 320, such as a laser, that emits an excitatory beam 20, 330. The excitatory beam 20, 330 interacts with the released nucleotides 16, 130 so that electrons are excited to a higher energy state. The Raman emission spectrum that results from the return of the electrons to a lower energy state is detected by a Raman spectroscopic detector 21, 310, such as a spectrometer, a monochromator or a charge coupled device (CCD), such as a CCD camera.

Preparation of Reaction Chamber and Flow Path

Borofloat glass wafers (Precision Glass & Optics, Santa Ana, Calif.) are pre-etched for a short period in concentrated HF (hydrofluoric acid) and cleaned before deposition of an amorphous silicon sacrificial layer in a plasma-enhanced chemical vapor deposition (PECVD) system (PEII-A, Technics West, San Jose, Calif.). Wafers are primed with hexamethyldisilazane (HMDS), spin-coated with photoresist (Shipley 1818, Marlborough, Mass.) and soft-baked. A contact mask aligner (Quintel Corp. San Jose, Calif.) is used to expose the photoresist layer with one or more mask designs, and the exposed photoresist removed using a mixture of Microposit developer concentrate (Shipley) and water. Developed wafers are hard-baked and the exposed amorphous silicon removed using $CF_4$ (carbon tetrafluoride) plasma in a PECVD reactor. Wafers are chemically etched with concentrated HF to produce the reaction chamber 11, 220 and flow path 12. The remaining photoresist is stripped and the amorphous silicon removed. Using these methods, microchannels of about 50 to 100 μm diameter may be prepared. Smaller diameter channels may be prepared by known methods, such as coating the inside of the microchannel to narrow the diameter, or using nanolithography, focused electron beam, focused ion beam or focused atom laser techniques.

Access holes are drilled into the etched wafers with a diamond drill bit (Crystalite, Westerville, Ohio). A finished chip is prepared by thermally bonding two complementary etched and drilled plates to each other in a programmable vacuum furnace (Centurion V P M, J. M. Ney, Yucaipa, Calif.). Alterative exemplary methods for fabrication of a chip incorporating a reaction chamber 11, 220 and flow path 12 are disclosed in U.S. Pat. Nos. 5,867,266 and 6,214,246. In certain embodiments of the invention, a nylon filter with a molecular weight cutoff of 2,500 daltons is inserted between the reaction chamber 11, 220 and the flow path 12 to prevent exonuclease 15 from leaving the reaction chamber 11, 220.

Nucleic Acid Preparation and Exonuclease Treatment

Human chromosomal DNA is purified according to Sambrook et al. (1989). Following digestion with Bam H1, the genomic DNA fragments are inserted into the multiple cloning site of the pBluescript® II phagemid vector (Stratagene, Inc., La Jolla, Calif.) and grown up in E. coli. After plating on ampicillin-containing agarose plates a single colony is selected and grown up for sequencing. Single-stranded DNA copies of the genomic DNA insert are rescued by co-infection with helper phage. After digestion in a solution of proteinase K:sodium dodecyl sulphate (SDS), the DNA is phenol extracted and then precipitated by addition of sodium acetate (pH 6.5, about 0.3 M) and 0.8 volumes of 2-propanol. The DNA containing pellet is resuspended in Tris-EDTA buffer and stored at −20° C. until use. Agarose gel electrophoresis shows a single band of purified DNA.

M13 forward primers complementary to the known pBluescript® sequence, located next to the genomic DNA insert, are purchased from Midland Certified Reagent Company (Midland, Tex.). The primers are covalently modified to contain a biotin moiety attached to the 5' end of the oligonucleotide. The biotin group is covalently linked to the 5'-phosphate of the primer via a $(CH_2)_6$ spacer. Biotin-labeled primers are allowed to hybridize to the ssDNA template molecules prepared from the pBluescript® vector. The primer-template complexes are then attached to streptavidine coated beads 14 according to Dorre et al. (Bioimaging 5:139–152, 1997). At appropriate DNA dilutions, a single primer-template complex is attached to a single bead 14. A bead 14 containing a single primer-template complex is inserted into the reaction chamber 11, 220 of a sequencing apparatus 10, 100, 210.

The primer-template is incubated with modified T7 DNA polymerase (United States Biochemical Corp., Cleveland, Ohio). The reaction mixture contains unlabeled deoxyadenosine-5'-triphosphate (dATP) and deoxyguanosine-5'-triphosphate(dGTP), digoxigenin-labeled deoxyuridine-5'-triphosphate(digoxigenin-dUTP) and rhodamine-labeled deoxycytidine-5'-triphosphate (rhodamine-dCTP). The polymerization reaction is allowed to proceed for 2 hours at 37° C. After synthesis of the digoxigenin and rhodamine labeled nucleic acid 13, the template strand is separated from the labeled nucleic acid 13, and the template strand, DNA polymerase and unincorporated nucleotides are washed out of the reaction chamber 11, 220.

Exonuclease 15 activity is initiated by addition of exonuclease III 15 to the reaction chamber 11, 220. The reaction mixture is maintained at pH 8.0 and 37° C. As nucleotides 16, 130 are released from the 3' end 17 of the nucleic acid 13, they are transported by microfluidic flow down the flow path 12 past the detection unit 18, 180, 300.

Detection of Labeled Nucleotides

The detection unit 18, 180, 300 comprises a laser 19, 320 and Raman detector 21, 310. The excitation beam 20, 330 is generated by a titanium:sapphire laser 19, 320 (Tsunami by Spectra-Physics) at a near-infrared wavelength (750~950 nm) or a galium aluminum arsenide diode laser 19, 320 (PI-ECL series by Process Instruments) at 785 nm or 830 nm. Pulsed laser beams 20, 330 or continuous beams 20, 330 can be used. The excitation beam 20, 330 is reflected by a dichroic mirror (holographic notch filter by Kaiser Optical or an interference filter by Chroma or Omega Optical) into a collinear geometry with the collected beam. The reflected beam passes a microscope objective (Nikon LU series), and is focused onto a micro-well, flow path (micro-channel) 12 or flow-through cell 170, 290 where target nucleotides 16, 130 are located. The Raman scattered light from the target nucleotides 16, 130 is collected by the same microscope objective, and passes the dichroic mirror to the Raman detector 21, 310. The Raman detector 21, 310 comprises a focusing lens, a spectrograph, and an array detector. The focusing lens focuses the Raman scattered light through the entrance slit of the spectrograph. The spectrograph (Roper-Scientific) comprises a grating that disperses the light by its wavelength. The dispersed light is imaged onto an array detector (back-illuminated deep-depletion CCD camera by RoperScientific). The array detector is connected to a controller circuit, which is connected to a computer for data transfer and control of the detector 21, 310 function.

The Raman detector 21, 310 is capable of detecting and identifying single nucleotides 16, 130 of dATP, dGTP, rhodamine-dCTP and digoxigenin-dUTP moving past the detector 21, 310. Data on the time course for labeled nucleotide detection is compiled and analyzed to obtain the sequence of the nucleic acid 13.

Example 2

Nucleic Acid Sequencing Using Covalent Attachment to Nanoparticles

Another exemplary embodiment of the invention is disclosed in FIG. 2. Nucleotides 16, 130 are released from a nucleic acid 13 by exonuclease 15 activity. In certain embodiments of the invention, the nucleotides 16, 130 are unlabeled. Such embodiments do not involve incorporation of labeled nucleotides into a complementary strand 13 using primers and polymerases. Rather, nucleic acids 13 directly purified from any organ, tissue and/or cell sample or obtained by known cloning methods may be directly sequenced. In some embodiments of the invention, a single molecule of single-stranded RNA or DNA 13 may be attached to a surface 14 and treated with an exonuclease 15. Released nucleotides 16, 130 travel down a flow path 12. The flow path 12 may be contiguous with or identical to a microfluidic channel 110, 160, 260, 280.

Nucleotides 16, 130 from the reaction chamber 11, 220 are mixed with gold and/or silver nanoparticles 140. Silver nanoparticles 140 are prepared according to Lee and Meisel (J. Phys. Chem. 86:3391–3395, 1982). Gold nanoparticles 140 are purchased from Polysciences, Inc. (Warrington, Pa.). Gold nanoparticles 140 are available from Polysciences, Inc. in 5, 10, 15, 20, 40 and 60 nm sizes. In the present non-limiting Example, 60 nm gold nanoparticles 140 are used.

Prior to exposure to nucleotides 16, 130, surface-modified nanoparticles 140 are coated with a silane, such as 3-glycidoxypropyltrimethoxysilane (GOP), a reactive linker compound. GOP contains a terminal highly reactive epoxide group. Nanoparticles 140 may be modified to contain hydroxyl groups to allow covalent attachment of GOP. The silanized nanoparticles 140 are mixed with nucleotides 16, 130 and allowed to form covalent cross-links with the nucleotides 16, 130. The nucleotide-nanoparticle complexes 150 pass through a flow through cell 170, 290 and are identified by SERS, SERRS and/or CARS using a Raman detection unit 18, 180, 300. Because of the close proximity of the nucleotides 16, 130 to the nanoparticles 140, the Raman signals are greatly enhanced, allowing detection of single nucleotides 16, 130 passing through the flow-through cell 170, 290.

Example 3

Apparatus for Nucleic Acid Sequencing

Figure 3:
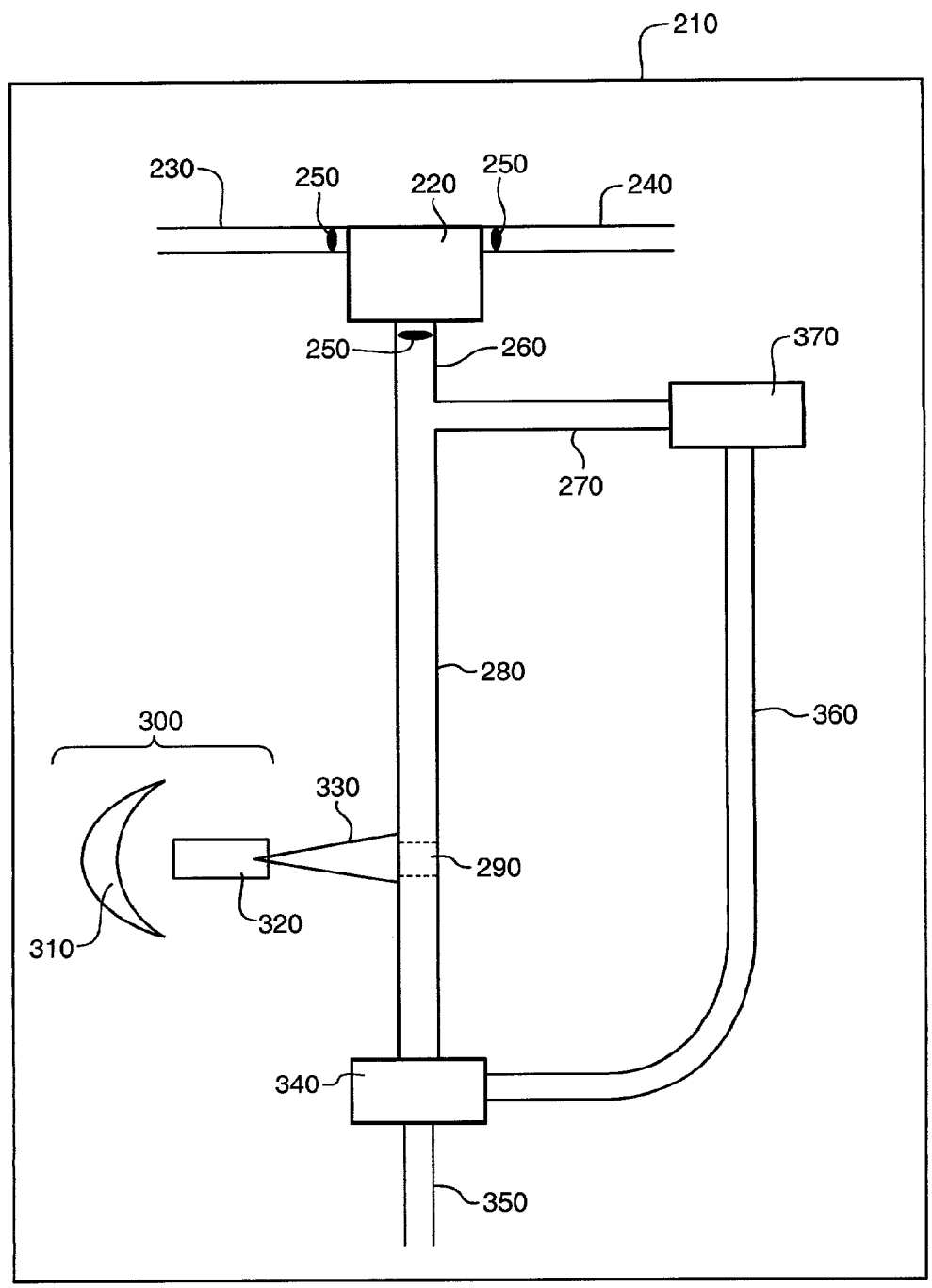
FIG. 3 illustrates another exemplary apparatus 210 (not to scale) for nucleic acid 13 sequencing.

FIG. 3 shows another exemplary embodiment of the invention. A DNA sequencing apparatus 10, 100, 210 comprises a reaction chamber 11, 220 in fluid communication with an influx channel 230 and an efflux channel 240. Fluid movement may be controlled through the use of one or more valves 250. A microfluidic channel 130, 260 is also in fluid communication with the reaction chamber 11, 220. Nucleotides 16, 130 released from one or more nucleic acids 13 by exonuclease 15 activity exit the reaction chamber 11, 220 through the microfluidic channel 110, 260. The nucleotides 16, 130 are mixed with nanoparticles 140 that move through a nanoparticle channel 120, 270 in fluid communication with the microfluidic channel 110, 260. Covalent attachment of nucleotides 16, 130 to nanoparticles 140 occurs within an attachment channel 160, 280. The covalently bound nucleotide-nanoparticle complexes 150 pass through a flow-through cell 170, 290 where the nucleotides 16, 130 are identified by a Raman detection unit 18, 180, 300. The detection unit 18, 180, 300 comprises a laser 19, 320 and Raman detector 21, 310. The laser emits an excitation beam 20, 330 that excites nucleotides 16, 130 within the flow-through cell 170, 290. Excited nucleotides 16, 130 emit a Raman signal that is detected by the Raman detector 21, 310.

In certain embodiments of the invention, nanoparticles 140 may be recovered in a recycling chamber 340. The nanoparticles are chemically treated, for example with acid solutions, and then washed to remove bound nucleotides 16, 130, linker compounds and any other attached or adsorbed molecules. The nanoparticles 140 may be recycled to a nanoparticle reservoir 370 via a recycling channel 360. In some embodiments of the invention, nanoparticles 140 may be coated with a linker compound, such as GOP, in the recycling channel 360 and/or the nanoparticle reservoir 370. Waste effluent is removed from the recycling chamber 340 via a waste channel 350.

All of the METHODS and APPARATUS disclosed and claimed herein can be made and executed without undue experimentation in light of the present disclosure. It will be apparent to those of skill in the art that variations may be applied to the METHODS and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A method comprising:
    a) obtaining nucleotides covalently linked to gold or silver, or gold and silver, nanoparticle(s), wherein the nucleotide and nanoparticle are linked via a terminal highly reactive cross-linking group selected from the group consisting of epoxide groups, azido groups, triazine groups, arylazido groups, and diazo groups;
    b) synthesizing a nucleic acid comprising the labeled nucleotides;
    c) immobilizing the nucleic acid of b) on a solid substrate;
    d) sequentially releasing nucleotides from one end of the nucleic acid;
    e) separating the released nucleotides from the immobilized nucleic acid by transferring the nucleotides through a microfluidic channel;
    f) identifying nucleotides by Raman spectroscopy; and
    g) determining the sequence of the nucleic acid.

2. The method of claim 1, wherein the microfluidic channel is a metal coated channel.

3. The method of claim 1, wherein only pyrimidine nucleotides are labeled with Raman labels.

4. The method of claim 1, further comprising: (i) obtaining at least one template nucleic acid molecule; (ii) hybridizing the template nucleic acid molecule to a primer; and (iii) adding a DNA polymerase to synthesize said nucleic acid.

5. The method of claim 1, wherein said nucleotides are removed from said nucleic acid by exonuclease activity.

6. The method of claim 5, wherein only one nucleic acid at a time is exposed to exonuclease activity.

7. The method of claim 1, wherein the Raman spectroscopy is surface enhanced Raman spectroscopy (SERS), surface enhanced resonance Raman spectroscopy (SERRS) and/or CARS.

* * * * *